United States Patent [19]

Burk et al.

[11] 4,093,644

[45] June 6, 1978

[54] 3-((4-(2,2-DICHLORO-1,1-DIFLUOROETHOXY)-2-METHYL-5-NITROPHENYL)SULFONYL)-2-PROPENENITRILE

[75] Inventors: George A. Burk, Bay City; Christian T. Goralski; Craig E. Mixan, both of Midland, all of Mich.

[73] Assignee: The Dow Chemical Company, Midland, Mich.

[21] Appl. No.: 770,862

[22] Filed: Feb. 22, 1977

[51] Int. Cl.$^2$ .................................... C07C 121/75
[52] U.S. Cl. ........................ 260/465 F; 260/543 R; 260/612 D; 424/304
[58] Field of Search ........................... 260/465 F

[56] References Cited

U.S. PATENT DOCUMENTS

| 3,159,532 | 12/1964 | Heininger et al. | 424/304 |
| 3,541,119 | 11/1970 | Richter et al. | 260/397.6 |
| 3,821,399 | 6/1974 | Richter | 424/304 |
| 4,049,696 | 9/1977 | Burk et al. | 260/465 F |

*Primary Examiner*—Dolph H. Torrence
*Attorney, Agent, or Firm*—Daniel L. DeJoseph; C. Kenneth Bjork

[57] ABSTRACT

The compound 3-((4-(2,2-dichloro-1,1-difluoroethoxy)-2-methyl-5-nitrophenyl)sulfonyl)-2-propenenitrile. The compound has antimicrobial activity.

1 Claim, No Drawings

3-((4-(2,2-DICHLORO-1,1-DIFLUOROETHOXY)-2-METHYL-5-NITROPHENYL)SULFONYL)-2-PROPENENITRILE

DESCRIPTION OF KNOWN PRIOR ART

U.S. Pat. No. 3,159,532 discloses phenylsulfonyl alkenenitriles such as 3-(4-chlorophenylsulfonyl)acrylonitrile and analogs thereof having on the phenyl nucleus other halo or lower alkyl substitution. U.S. Pat. No 3,541,119 discloses benzenesulfonylacrylonitrile and homologs and analogs thereof having halo or lower alkyl or p-acetamido substitution on the benzene nucleus. U.S. Pat. No. 3,821,399 discloses phenylsulfonylacrylonitriles wherein the phenyl moiety has at least one substituent selected from amino, acrylamide or nitro and, optionally, a second lower alkyl substituent on the phenyl moiety. The compounds disclosed in the above-cited patents are said to have bioactive properties.

SUMMARY OF THE INVENTION

The novel compound 3-((4-(2,2-dichloro-1,1-difluoroethoxy)-2-methyl-5-nitrophenyl)sulfonyl)-2-propenenitrile, hereinafter alternatively referred to as "Compound", having the formula

is prepared by mixing together in a reaction vessel one molar proportion of 4-(2,2-dichloro-1,1-difluoroethoxy)-2-methyl-5-nitrobenzenesulfonyl chloride with substantially two molar proportions of acrylonitrile in the presence of acetonitrile, cupric chloride, and triethylamine hydrochloride. The reaction vessel is cooled, evacuated to about 5 mm mercury pressure, and heated from about 105°–110° C until the reaction is substantially complete; usually from about 30 to about 40 hours. The reaction medium is filtered with the aid of benzene, and the filtrate is treated with triethylamine, refiltered and washed. After drying over $MgSO_4$, the solvent is removed under pressure to give a dark amber oil, which upon recrystallization from methanol gives the title compound as a white solid, melting at 109° C.

PREPARATION OF THE STARTING MATERIAL 4-(2,2-Dichloro-1,1-difluoroethoxy)-2-methyl-5-nitrobenzenesulfonyl chloride is prepared in the following two-step process.

A.
2-(2,2-Dichloro-1,1-difluoroethoxy)-4-methyl-1-nitrobenzene

In a 500 ml stirred reaction flask equipped with thermometer, air condenser, dropping funnel and ice water bath was placed 76.57 g (0.5 mol) of 5-methyl-2-nitrophenol in 150 ml of acetone and 5.5 g of powdered KOH (85 percent). The mixture was vigorously stirred at 10° C, whereupon 73 g of 2,2-dichloro-1,1-difluoroethene was gradually introduced. After stirring overnight, the reaction mixture was poured into ice water, and the lower organic layer separated by methylene chloride extraction. The extract was washed with diluted bicarbonate of soda solution, decolorized with charcoal, and dried over desiccant-grade magnesium sulfate. Evaporation of the solvent left an oily residue which was vacuum distilled at 5 mm to give 38.6 g of 2-(2,2-dichloro-1,1-difluoroethoxy)-4-methyl-1-nitrobenzene distilling at 156° C.

B.
4-(2,2-Dichloro-1,1-difluoroethoxy)-2-methyl-5-nitrobenzenesulfonyl chloride In a 500 ml stirred reaction flask equipped with thermometer, air condenser, dropping funnel and ice water bath was placed 50 ml of chlorosulfonic acid, and, while stirring at 0° to 10° C, there was added dropwise over a one-half hour period 17.2 g of 2-(2,2-dichloro-1,1-difluoroethoxy)-4-methyl-1-nitrobenzene. After stirring for 50 hours, the reaction mixture was poured over crushed ice. The organic phase was extracted with methylene chloride, and the extract was washed with dilute bicarbonate, decolorized with charcoal and dried. Evaporation of the solvent affored 10 g of 4-(2,2-dichloro-1,1-difluoroethoxy)-2-methyl-5-nitrobenzenesulfonyl chloride as a solid melting at 60°–61° C.

The following example describes a representative specific embodiment of the preparation of the compound of this invention. The product Compound was identified by elemental analysis and nuclear magnetic resonance spectroscopy.

EXAMPLE

3-((4-(2,2-Dichloro-1,1-difluoroethoxy)-2-methyl-5-nitrophenyl)sulfonyl)-2-propenenitrile In a 100 ml Fisher-Porter pressure vessel were placed 9.0 g (0.024 mol) of 4-(2,2-dichloro-1,1-difluoroethoxy)-2-methyl-5-nitrobenzenesulfonyl chloride, 2.4 g (0.048 mol) acrylonitrile, 2 ml acetonitrile, 0.07 g cupric chloride and 0.12 g triethylamine hydrochloride. After cooling and evacuating the vessel to 5 mm mercury pressure, it was sealed and heated in an oil bath at 105°–110° C for 38 hours. The vessel was opened and the reaction medium was filtered with the aid of benzene. The insolubles were discarded and the filtrate was treated with 5.0 g of triethylamine, refiltered, and washed with water. After decolorizing wth charcoal and drying over $MgSO_4$, removal of the solvent under reduced pressure afforded a dark amber oil. Recrystallization from methanol provided 1.0 g of the title compound as a white solid, m.p. 109° C.

Anal. Calculated for $C_{12}H_9Cl_2F_2N_2O_5S$: C, 35.94; H, 2.0; N, 6.98. Found: C, 36.1; H, 2.06; N, 7.03.

The Compound of the present invention has exhibited antimicrobial activity. In representative activity tests, the Compound is dispersed in warm melted nutrient agar which is then poured into Petri dishes and allowed to soldify, the Compound being employed in an amount sufficient to provide from 0.5 to 500 parts by weight thereof per million parts (ppm) of the ultimate agar composition. The surface of the agar was then inoculated with a variety of bacterial and fungal pest organisms, and the inoculated plates were incubated under conditions conducive to bacterial and fungal growth. Similar check plates in which the agar does not contain the Compound or other toxic compounds were similarly inoculated and incubated.

In such operations, the Compound gave 100 percent growth inhibition (kill) and control of the following organisms at the indicated concentrations in parts per million:

TABLE
Antimicrobial Activity 3-((4-(2,2-Dichloro-1,1-difluoroethoxy)-2-methyl-5-nitrophenyl)-sulfonyl)-2-propenenitrile

| Organism | Conc. in ppm |
| --- | --- |
| S. aureus | 5 |
| C. albicans | 50 |
| T. mentagrophytes | 5 |
| P. chrysogenum | 10 |

TABLE-continued
Antimicrobial Activity 3-((4-(2,2-Dichloro-1,1-difluoroethoxy)-2-methyl-5-nitrophenyl)-sulfonyl)-2-propenenitrile

| Organism | Conc. in ppm |
| --- | --- |
| A. niger | 50 |
| B. subtilis | 0.5 |
| C. pelliculosa | 50 |
| P. pullulans | 50 |
| S. typhosa | 10 |
| C. ips | 50 |
| T. Sp. Madison P-42 | 50 |
| T. Sp. Med. Col. VI | 50 |
| A. fumig. Med. Col. VI | 50 |
| C. albicans NIH | 50 |

What is claimed is:
1. The compound 3-((4-(2,2-dichloro-1,1-difluoroethoxy)-2-methyl-5-nitrophenyl)sulfonyl)-2-propenenitrile.

* * * * *

UNITED STATES PATENT AND TRADEMARK OFFICE
CERTIFICATE OF CORRECTION

PATENT NO. : 4,093,644
DATED : June 6, 1978
INVENTOR(S) : George A. Burk, et al.

It is certified that error appears in the above-identified patent and that said Letters Patent are hereby corrected as shown below:

Column 1, line 47 "under pressure" should read -- under reduced pressure";

Column 2, line 23 "affored" should read -- afforded --;

Column 2, line 59 "soldify" should read -- solidify --;

Column 3, "TABLE" first line of title should read -- Antimicrobial Activity of 3-((4-(2,2-Dichloro-1,1- --.

Signed and Sealed this

Nineteenth Day of December 1978

[SEAL]

Attest:

RUTH C. MASON
Attesting Officer

DONALD W. BANNER
Commissioner of Patents and Trademarks